US00PP37080P2

(12) United States Plant Patent
Meilland

(10) Patent No.: US PP37,080 P2
(45) Date of Patent: Nov. 4, 2025

(54) FLORIBUNDA ROSE PLANT NAMED 'Meiscouby'

(50) Latin Name: *Rosa hybrida*
Varietal Denomination: Meiscouby

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/978,881

(22) Filed: Dec. 12, 2024

(51) Int. Cl.
*A01H 5/02* (2018.01)
*A01H 6/74* (2018.01)

(52) U.S. Cl.
USPC ..... Plt./149

(58) Field of Classification Search
USPC ..... Plt./141, 147, 148, 149
See application file for complete search history.

(56) References Cited

U.S. PATENT DOCUMENTS

| | | | |
|---|---|---|---|
| PP3,846 | P | 3/1976 | Kordes |
| PP5,002 | P | 3/1983 | Warriner |
| PP17,518 | P3 | 3/2007 | Cowlishaw |

*Primary Examiner* — Susan Mccormick Ewoldt
*Assistant Examiner* — Zachariah Allan Kay
(74) *Attorney, Agent, or Firm* — Panitch Schwarze Belisario & Nadel LLP; Stephany G. Small; Travis W. Bliss

(57) ABSTRACT

A new and distinct variety of floribunda rose plant, referred to by its cultivar name, 'Meiscouby', is described. The new variety forms in abundance on a substantially continuous basis, purple-magenta-colored blossoms. The growth habit is bushy and upright. Matte, medium green ornamental foliage is formed. Additionally, the new variety is particularly well suited for growing as ornamentation in the landscape.

1 Drawing Sheet

Latin name of genus and species of plant claimed: *Rosa hybrida.*

Variety denomination: 'Meiscouby'.

BACKGROUND OF THE INVENTION

The new variety of floribunda rose plant of the present invention was created by controlled breeding during May 2003, in Le Cannet de Maures, France by artificial pollination wherein two parents were crossed which previously had been studied in the hope that they would contribute the desired characteristics. The female parent (i.e., the seed parent) of the new variety an unnamed seedling that was the product of the cross between the 'KORblue' variety (U.S. Plant Pat. No. 3,846) and the 'Delboip' variety (not patented). The male parent (i.e., the pollen parent) of the new variety was the 'FRAntasia' variety (U.S. Plant Pat. No. 17,518).

The parentage of the new variety can be summarized as follows:

('KORblue' x 'Delboip') x 'FRAntasia'

The seeds resulting from the above pollination were sown and small plants were obtained which were physically and biologically different from each other. Selective study resulted in the identification of a single plant of the new variety.

The new variety has been found to undergo asexual propagation in Wasco, California by a number of routes such as budding. Asexual propagation techniques in Wasco, California, such as budding, have shown that the characteristics of the new variety are homogeneous, stable, and strictly transmissible by such asexual propagation from one generation to another. Accordingly, the new variety undergoes asexual propagation in a true-to-type manner.

SUMMARY OF THE INVENTION

It was found that the new variety of floribunda rose plant of the present invention possesses the following combination of characteristics:

(a) forms purple-magenta-colored blossoms,
(b) forms ornamental matte, medium green foliage, and
(c) exhibits a bushy and upright growth habit.

The new variety well meets the needs of the horticultural industry. It can be grown to advantage as ornamentation in parks, gardens, public areas, and residential landscapes. Accordingly, it is particularly well suited for growing in the landscape.

The new variety can be readily distinguished from its ancestors. More specifically, the new variety displays a deeper flower color compared to the unnamed seedling female parent (i.e., the product of ('KORblue' x 'Delboip')). Additionally, the new variety exhibits a higher petal count and larger flower diameter compared to the 'FRAntasia' variety (i.e., the pollen parent). Moreover, the new variety can be readily distinguished from non-parental related similar varieties. For example, the new variety blooms earlier and has a faster repeat bloom compared to the 'JACum' variety (U.S. Plant Pat. No. 5,002).

The new variety has been named the 'Meiscouby' variety.

BRIEF DESCRIPTION OF THE PHOTOGRAPHS

The accompanying photograph shows, as nearly true as it is reasonably possible to make the same in a color illustration of this character, a typical specimen of the new variety. The illustrated rose plant of the new variety was approximately two years of age and was grown under typical nursey production conditions in a three-gallon container in Cochranville, Pennsylvania in May 2024.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms and The R.H.S. Colour Chart designation used herein represents the closest color observed on the majority of the specified botanical feature. The description is based on a two-year-old specimen of the new variety, observed during May 2024, while growing on understock in a three-gallon container in a nursery in Cochranville, Pennsylvania.

Botanical classification: *Rosa hybrida* cultivar 'Meiscouby'.

Commercial classification: Floribunda Rose.

Plant:

*Habit*.—Bushy and upright.

*Height*.—Approximately 60.0 cm on average from the top of the soil plane.

*Width*.—Approximately 60.0 cm on average.

Branches:

*Stem color*.—Old wood: Yellow-Green Group 146B. — young stems: Green Group 143A.

*Length*.—Main stems: approximately 60.0 cm on average. — secondary stems: approximately 35.0 cm on average.

*Diameter*.—Main stems: approximately 1.0 cm on average. — secondary stems: approximately 5.0 mm on average.

*Prickles*.—Young prickles: length is approximately 5.0 mm on average; width is approximately 5.0 mm on average at point of attachment; and color is Greyed-Orange Group 173A at point of attachment fading to Greyed-Yellow Group 161A. — old prickles: length is approximately 1.0 cm on average; width is approximately 1.0 cm on average at point of attachment; and color is Greyed-Orange Group 173A.

Leaflets:

*Number*.—5 and 7.

*Shape*.—Ovate; apex is acute to acuminate; and base is cuneate.

*Arrangement*.—Odd-pinnate.

*Margin*.—Serrate.

*Glossiness of upper side*.—Matte.

*Texture*.—Upper surface: smooth. — under surface: smooth.

*Venation pattern*.—Reticulate.

*Size*.—Terminal leaflet: length is approximately 6.0 cm on average; width is approximately 4.5 cm on average. — lower leaflets: length is approximately 4.0 to 5.0 cm on average; width is approximately 3.0 to 3.5 cm on average. — 5-Leaflet leaf: length is approximately 14.0 cm on average; width is approximately 11.5 cm on average.

Foliage:

*Young foliage*.—Upper surface color: Green Group 137A with venation of Green Group 137C. — under surface color: Green Group 138A with indistinguishable venation.

*Old foliage*.—Upper surface color: Green Group 137A with slight venation of Yellow-Green Group 144A. — under surface color: Green Group 137B with indistinguishable venation.

*Petiole*.—Texture: upper surface is hispidulous; under surface is smooth. — length: approximately 2.5 cm on average. — width: approximately 1.0 mm on average. — upper surface color: Green Group 143A. — under surface color: Green Group 143C.

*Rachis*.—Length: approximately 6.0 cm on average. — width: approximately 1.0 mm on average. — upper surface color: Yellow-Green Group 144A. — under surface color: Yellow-Green Group 144B.

*Stipules*.—Length: approximately 2.3 cm on average. — width: approximately 7.0 mm on average. — margin: entire to erose. — upper surface color: Yellow-Green Group 144A. — lower surface color: Yellow-Green Group 146B.

Inflorescence:

*Number of flowers*.—About 20 to 25 blooms on average on a plant at once.

*Number of blossoms per stem or in a cluster*.—Typically 1 to 5 blooms per stem on average.

*Peduncle*.—Color: Yellow-Green Group 144A. — diameter: approximately 2.0 mm on average. — length: approximately 5.5 cm on average. — surface texture: holosericeous.

*Sepals*.—Number: 5. — upper surface color and texture: Green Group 138A, covered in short pubescence. — under surface color and texture: Green Group 138B, puberulent. — size: length is approximately 4.0 cm on average; width is approximately 1.0 mm on average. — margin: entire with extensions on most sepals measuring approximately 5.0 mm in length and 1.0 mm in width on average. — apex: acute to aristate. — base: truncate as it joins the receptacle.

*Buds*.—Shape: ovoid. — size: length is approximately 2.7 cm on average; width is approximately 1.5 cm on average. — color (when opening): Red-Purple Group 64A.

*Flower*.—Form: double, cuplike. — profile: concave as it opens, and then outer petals are convex as the bloom ages and opens further. — diameter: approximately 10.0 cm on average. — height: approximately 4.0 cm on average. — duration: on the plant approximately 10 to 12 days. — petal color when first and fully opened: upper surface is Red-Purple Group 72A to Red-Purple Group 72B with a basal spot of White Group NN155C and Yellow-White Group 158A; under surface is Purple Group 77B with a basal spot of White Group 155A. — petal color at end of bloom: upper surface is Purple Group N78A with a basal spot of White Group 155A; under surface is Purple-Violet Group N80C with a basal spot of White Group 155A. — petals reflex one by one: yes.

*Fragrance*.—Strong sweet scent.

*Petal*.—Number: 30 on average. — length: 4.6 cm on average. — width: 5.5 cm on average. — overall shape: broadly obovate. — apex shape: rounded to slightly reniform. — base shape: cuneate. — texture: upper surface is smooth; under surface is smooth.

*Petaloids*.—Number: approximately 4 on average. — length: approximately 3.3 cm on average. — width: approximately 1.0 cm on average. — color: upper and under surfaces are Purple Group N78A with a basal spot of Red-Purple Group 62D. — texture: smooth. — apex: obovate. — base: linear.

*Stamen*.—Number: approximately 100. — anthers: number is approximately 100; color is Greyed-Orange Group 163B; length is approximately 3.0 mm on average; and shape is oval. — filaments: length is approximately 6.0 mm on average and color is Yellow-White Group 158A.

*Pistils*.—Arrangement: separate and free. — number: approximately 70. — style: length is approximately 5.0 mm on average and color is Greyed-Red Group 182C. — stigma: diameter is approximately 1.0 mm on average; shape is fan shaped; color is Yellow Group BB.

*Receptacle*.—Diameter: approximately 8.0 mm on average. — depth: approximately 1.0 cm on average. — shape: urn shaped. — color: Yellow-Green Group 144A. — surface texture: smooth.

*Pollen*.—Amount: moderate. — color: Yellow-Orange Group 20A

*Hips/seed*.—None observed.

Development:

*Vegetation*.—Matte, medium green.

*Blossoming*.—Abundant and continuous from spring through frost; typically, in bloom outdoors from May to November in Southeastern Pennsylvania.

*Resistance to diseases*.—Good resistance to powdery mildew (*Sphaerotheca pannosa*).

*Hardiness*.—Hardy to USDA Zone 6.

The new 'Meiscouby' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of floribunda rose plant named 'Meiscouby' characterized by the following combination of characteristics:

(a) forms purple-magenta-colored blossoms, (b) forms ornamental matte, medium green foliage, and (c) exhibits a bushy and upright growth habit;

substantially as herein shown and described.

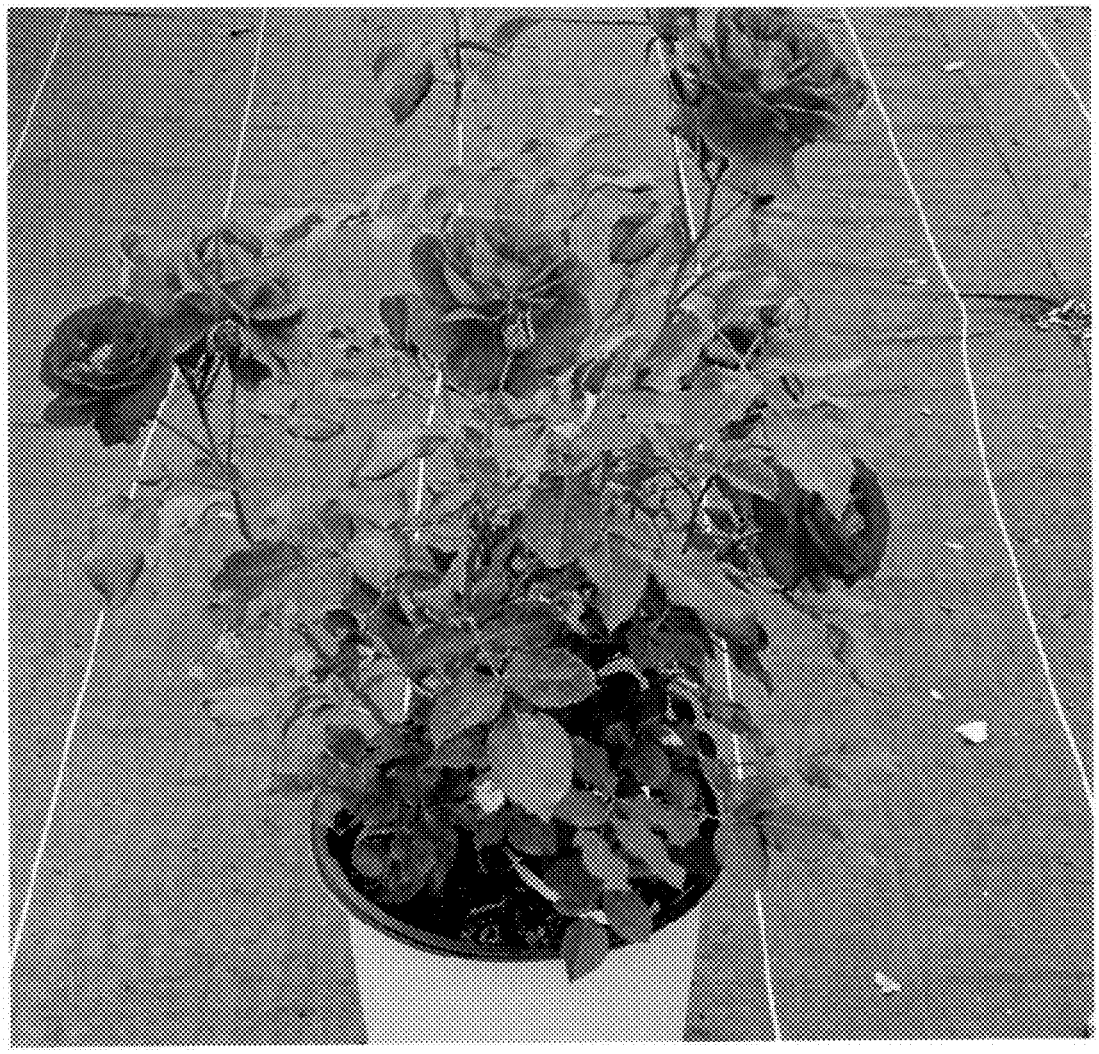

* * * * *